United States Patent
Huang et al.

(10) Patent No.: US 12,152,255 B2
(45) Date of Patent: Nov. 26, 2024

(54) ω-TRANSAMINASE MUTANT OBTAINED BY DNA SYNTHETIC SHUFFLING COMBINED MUTATION AND USE

(71) Applicants: ZHEJIANG UNIVERSITY OF SCIENCE & TECHNOLOGY, Hangzhou (CN); ENZYMASTER (NINGBO) BIO-ENGINEERING CO., LTD., Ningbo (CN)

(72) Inventors: Jun Huang, Hangzhou (CN); Chunyan Liu, Hangzhou (CN); Lehe Mei, Hangzhou (CN); Haibin Chen, Ningbo (CN); Changjiang Lv, Hangzhou (CN); Sheng Hu, Hangzhou (CN); Hongpeng Wang, Hangzhou (CN); Weirui Zhao, Hangzhou (CN); Fangfang Fan, Hangzhou (CN); Ye Li, Hangzhou (CN); Linka Yu, Hangzhou (CN); Yifeng Zhou, Hangzhou (CN)

(73) Assignees: ZHEJIANG UNIVERSITY OF SCIENCE & TECHNOLOGY, Hangzhou (CN); ENZYMASTER (NINGBO) BIO-ENGINEERING CO., LTD., Ningbo (CN)

( * ) Notice: Subject to any disclaimer, the term of this patent is extended or adjusted under 35 U.S.C. 154(b) by 0 days.

(21) Appl. No.: 17/543,608

(22) Filed: Dec. 6, 2021

(65) Prior Publication Data

US 2022/0177933 A1    Jun. 9, 2022

(30) Foreign Application Priority Data

Dec. 4, 2020   (CN) ......................... 2020114150071.1

(51) Int. Cl.
*C12N 9/10* (2006.01)
*C12N 15/63* (2006.01)
(Continued)

(52) U.S. Cl.
CPC ........... *C12N 9/1096* (2013.01); *C12N 15/63* (2013.01); *C12P 7/26* (2013.01); *C12N 15/1027* (2013.01);
(Continued)

(58) Field of Classification Search
CPC .................................................. C12N 9/1096
See application file for complete search history.

(56) References Cited

FOREIGN PATENT DOCUMENTS

| CN | 108913671 A | * | 11/2018 | ............. | C12N 15/70 |
| CN | 110144335 A | * | 8/2019 | ........... | C12N 9/1096 |

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Jiwen Chen; Joywin IP Law PLLC

(57) ABSTRACT

The present invention discloses a ω-transaminase mutant obtained through DNA synthetic shuffling combined mutation. The ω-transaminase mutant is obtained through point mutation of a wild type ω-transaminase from *Aspergillus terrus*. The amino acid sequence of the wild type ω-transaminase is shown in SEQ ID NO: 1. The mutation site of the ω-transaminase mutant is any one of: (1) F115L-H210N-M150C-M280C; (2) F115L-H210N; (3) F115L-H210N-E253A-I295V; (4) I77L-F115L-E133A-H210N-N245D; (5) I77L-Q97E-F115L-L118T-E253A-G292D; (6) I77L-E133A-N245D-G292D; and (7) H210N-N245D-E253A-G292D. According to the present invention, forward mutations obtained in the previous stage are randomly combined through a DNA synthetic shuffling combined mutation method. It is verified through experiments that this (Continued)

method can effectively improve the probability of forward mutation and increase experimental efficiency and feasibility, and is capable of obtaining mutant enzymes with thermodynamic stability remarkably superior to that of wild enzymes via screening.

4 Claims, 5 Drawing Sheets

Specification includes a Sequence Listing.

(51) Int. Cl.
*C12P 7/26* (2006.01)
*C12N 15/10* (2006.01)
*C12R 1/19* (2006.01)
*C12R 1/66* (2006.01)

(52) U.S. Cl.
CPC ...... *C12R 2001/19* (2021.05); *C12R 2001/66* (2021.05); *C12Y 206/01018* (2013.01)

(56) References Cited

OTHER PUBLICATIONS

A0A094CG71. UniProtKB/TrEMBL Database. Nov. 26, 2014.*
Machine English Translation of CN 108913671 A. retrieved on Feb. 15, 2023.*
Machine English Translation of CN 110144335 A. retrieved on Feb. 15, 2023.*

* cited by examiner

SEQUENCE LISTING

<160> NUMBER OF SEQ ID NOS: 41

<210> SEQ ID NO 1
<211> LENGTH: 325
<212> TYPE: PRT
<213> ORGANISM: Aspergillus terreus

<400> SEQUENCE: 1

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

```
Val Trp Asp Gly Arg Phe Phe Arg Leu Asp Asp His Ile Thr Arg Leu
 65                  70                  75                  80

Glu Ala Ser Cys Thr Lys Leu Arg Leu Arg Leu Pro Leu Pro Arg Asp
                 85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
            180                 185                 190

Glu Ala Ala Asp Arg Gly Ala Thr Tyr Pro Phe Leu Thr Asp Gly Asp
        195                 200                 205

Ala His Leu Thr Glu Gly Ser Gly Phe Asn Ile Val Leu Val Lys Asp
    210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

Glu Phe Val Pro Val Glu Leu Ala Tyr Arg Cys Asp Glu Ile Phe Met
            260                 265                 270

Cys Thr Thr Ala Gly Gly Ile Met Pro Ile Thr Thr Leu Asp Gly Met
        275                 280                 285

Pro Val Asn Gly Gly Gln Ile Gly Pro Ile Thr Lys Lys Ile Trp Asp
    290                 295                 300

Gly Tyr Trp Ala Met His Tyr Asp Ala Ala Tyr Ser Phe Glu Ile Asp
305                 310                 315                 320

Tyr Asn Glu Arg Asn
                325

<210> SEQ ID NO 2
<211> LENGTH: 978
<212> TYPE: DNA
<213> ORGANISM: Aspergillus terreus

<400> SEQUENCE: 2
atggccagta tggataaggt ttttgcaggc tatgctgccc gtcaagcaat cttagaaagt      60
accgaaacta cgaacccgtt tgccaaagga attgcctggg tcgaaggggg actcgttcct     120
ttagctgaag cacgcattcc actcctcgat cagggcttca tgcactccga tctgacctac     180
gacgtaccgt ctgtttggga tggcgatttt tttcgtttag atgatcatat tacacgcctg     240
gaagcaagct gcaccaagct gaggctgcgt ctacccttac acgtgatca gttaaacaa      300 atcctggtgg aaatggtcgc aaaatctggt attcggatg catttgttga attgatagtc     360
acccgcggtc ttaaagggt gcgaggaact cgtccgcatg atatagtgaa caacctgtac     420
atgtttgtgc agccgtacgt gtgggttatg gagccggata tgcagcgcgt aggcggcagc     480
gcagtggtgg ctaggaccgt ccgccgggta ccaccgggcg ctattgatcc gaccgtcaag     540
aatcttcagt ggggtgatct tgttcgtgga atgtttgaag cggctgatcg tggcgcaaca     600
```

```
tatcccttcc ttaccgacgg cgatgcgcac ctgactgaag gatcgggttt taatatagta    660
ttagtcaaag atggcgtcct gtatacgcca gatcgcgggg tgctgcaggg agtgactcgc    720
aagtccgtta tcaacgctgc tgaagccttt ggaatagaag tgcgggttga gttcgttcca    780
gttgagctgg cctaccggtg tgacgagatt ttcatgtgca cgacggcggg tggcattatg    840
cctatcacaa cattggacgg tatgcctgta aatggtgggc aaattgggcc tattacgaaa    900
aaaatatggg acggttattg ggcgatgcat tatgacgccg cgtattcgtt cgagatcgac    960
tataatgaga gaaattag                                                  978
```

<210> SEQ ID NO 3
<211> LENGTH: 978
<212> TYPE: DNA
<213> ORGANISM: Artificial Sequence
<220> FEATURE:
<223> OTHER INFORMATION: Synthesized

<400> SEQUENCE: 3

```
atggccagta tggataaggt ttttgcaggc tatgctgccc gtcaagcaat cttagaaagt     60
accgaaacta cgaacccgtt tgccaaagga attgcctggg tcgaagggga actcgttcct    120
ttagctgaag cacgcattcc actcctcgat cagggcttca tgcactccga tctgacctac    180
gacgtaccgt ctgtttggga tgggcgattt tttcgtttag atgatcatat tacacgcctg    240
gaagcaagct gcaccaagct gaggctgcgt ctacccttac cacgtgatca agttaaacaa    300
atcctggtgg aaatggtcgc aaaatctggt attcgggatg cattagttga attgatagtc    360
acccgcggtc ttaaaggggt gcgaggaact cgtccggaag atatagtgaa caacctgtac    420
atgtttgtgc agccgtacgt gtgggtttgc gagccggata tgcagcgcgt aggcggcagc    480
gcagtggtgg ctaggaccgt ccgccgggta ccaccgggcg ctattgatcc gaccgtcaag    540
aatcttcagt ggggtgatct tgttcgtgga atgtttgaag cggctgatcg tggcgcaaca    600
tatcccttcc ttaccgacgg cgatgcgaac ctgactgaag gatcgggttt taatatagta    660
ttagtcaaag atggcgtcct gtatacgcca gatcgcgggg tgctgcaggg agtgactcgc    720
aagtccgtta tcaacgctgc tgaagccttt ggaatagcgg tgcgggttga gttcgttcca    780
gttgagctgg cctaccggtg tgacgagatt ttcatgtgca cgacggcggg tggcatttgc    840
cctatcacaa cattggacgg tatgcctgta aatggtgggc aaattgggcc tattacgaaa    900
aaaatatggg acggttattg ggcgatgcat tatgacgccg cgtattcgtt cgagatcgac    960
tataatgaga gaaattag                                                  978
```

<210> SEQ ID NO 4
<211> LENGTH: 978
<212> TYPE: DNA
<213> ORGANISM: Artificial Sequence
<220> FEATURE:
<223> OTHER INFORMATION: Synthesized

<400> SEQUENCE: 4

```
atggccagta tggataaggt ttttgcaggc tatgctgccc gtcaagcaat cttagaaagt     60
accgaaacta cgaacccgtt tgccaaagga attgcctggg tcgaagggga actcgttcct    120
ttagctgaag cacgcattcc actcctcgat cagggcttca tgcactccga tctgacctac    180
gacgtaccgt ctgtttggga tgggcgattt tttcgtttag atgatcatat tacacgcctg    240
gaagcaagct gcaccaagct gaggctgcgt ctacccttac cacgtgatca agttaaacaa    300
```

```
atcctggtgg aaatggtcgc aaaatctggt attcggatg cattagttga attgatagtc      360
acccgcggtc ttaaaggggt gcgaggaact cgtccggaag atatagtgaa caacctgtac      420
atgtttgtgc agccgtacgt gtgggttatg gagccggata tgcagcgcgt aggcggcagc      480
gcagtggtgg ctaggaccgt ccgccgggta ccaccgggcg ctattgatcc gaccgtcaag      540
aatcttcagt ggggtgatct tgttcgtgga atgtttgaag cggctgatcg tggcgcaaca      600
tatcccttcc ttaccgacgg cgatgcgaac ctgactgaag gatcgggttt taatatagta      660
ttagtcaaag atggcgtcct gtatacgcca gctcgcgggg tgctgcaggg agtgactcgc      720
aagtccgtta tcaacgctgc tgaagccttt ggaatagaag tgcgggttga gttcgttcca      780
gttgagctgg cctaccggtg tgacgagatt ttcatgtgca cgacggcggg tggcattatg      840
cctatcacaa cattggacgg tatgcctgta aatggtgggc aaattgggcc tattacgaaa      900
aaaatatggg acggttattg ggcgatgcat tatgacgccg cgtattcgtt cgagatcgac      960
tataatgaga gaaattag                                                     978

<210> SEQ ID NO 5
<211> LENGTH: 978
<212> TYPE: DNA
<213> ORGANISM: Artificial Sequence
<220> FEATURE:
<223> OTHER INFORMATION: Synthesized

<400> SEQUENCE: 5
atggccagta tggataaggt ttttgcaggc tatgctgccc gtcaagcaat cttagaaagt       60
accgaaacta cgaacccgtt tgccaaagga attgcctggg tcgaagggga actcgttcct      120
ttagctgaag cacgcattcc actcctcgat cagggcttca tgcactccga tctgacctac      180
gacgtaccgt ctgtttggga tgggcgattt tttcgtttag atgatcatat tacacgcctg      240
gaagcaagct gcaccaagct gaggctgcgt ctacccttac cacgtgatca agttaaacaa      300
atcctggtgg aaatggtcgc aaaatctggt attcggatg cattagttga attgatagtc      360
acccgcggtc ttaaaggggt gcgaggaact cgtccgcaag atatagtgaa caacctgtac      420
atgtttgtgc agccgtacgt gtgggttatg gagccggata tgcagcgcgt aggcggcagc      480
gcagtggtgg ctaggaccgt ccgccgggta ccaccgggcg ctattgatcc gaccgtcaag      540
aatcttcagt ggggtgatct tgttcgtgga atgtttgaag cggctgatcg tggcgcaaca      600
tatcccttcc ttaccgacgg cgatgcgcaa ctgactgaag gatcgggttt taatatagta      660
ttagtcaaag atggcgtcct gtatacgcca gatcgcgggg tgctgcaggg agtgactcgc      720
aagtccgtta tcaacgctgc tgaagccttt ggaatagcag tgcgggttga gttcgttcca      780
gttgagctgg cctaccggtg tgacgagatt ttcatgtgca cgacggcggg tggcattatg      840
cctatcacaa cattggacgg tatgcctgta aatggtgggc aagttgggcc tattacgaaa      900
aaaatatggg acggttattg ggcgatgcat tatgacgccg cgtattcgtt cgagatcgac      960
tataatgaga gaaattag                                                     978

<210> SEQ ID NO 6
<211> LENGTH: 978
<212> TYPE: DNA
<213> ORGANISM: Artificial Sequence
<220> FEATURE:
<223> OTHER INFORMATION: Synthesized

<400> SEQUENCE: 6
atggccagta tggataaggt ttttgcaggc tatgctgccc gtcaagcaat cttagaaagt       60
```

```
accgaaacta cgaacccgtt tgccaaagga attgcctggg tcgaaggggaa actcgttcct      120 ttagctgaag cacgcattcc actcctcgat cagggcttca tgcactccga tctgacctac      180
gacgtaccgt ctgtttggga tgggcgattt tttcgtttag atgatcatct tacacgcctg     240
gaagcaagct gcaccaagct gaggctgcgt ctacccttac cacgtgatca agttaaacaa      300
atcctggtgg aaatggtcgc aaaatctggt attcgggatg cattagttga attgatagtc      360
acccgcggtc ttaaaggggt gcgaggaact cgtccggcag atatagtgaa caacctgtac      420
atgtttgtgc agccgtacgt gtgggttatg gagccggata tgcagcgcgt aggcggcagc      480
gcagtggtgg ctaggaccgt ccgccgggta ccaccgggcg ctattgatcc gaccgtcaag      540
aatcttcagt ggggtgatct tgttcgtgga atgtttgaag cggctgatcg tggcgcaaca      600
tatcccttcc ttaccgacgg cgatgcgaac ctgactgaag gatcgggttt taatatagta      660
ttagtcaaaa aaggcgtcct gtatacgcca gatcgcgggg tgctgcaggg agtgactcgc      720
aagtccgtta tcgacgctgc tgaagccttt ggaatagaag tgcgggttga gttcgttcca      780
gttgagctgg cctaccggtg tgacgagatt ttcatgtgca cgacggcggg tggcattatg      840
cctatcacaa cattggacgg tatgcctgta aatggtgggc aaattgggcc tattacgaaa      900
aaaatatggg acggttattg ggcgatgcat tatgacgccg cgtattcgtt cgagatcgac      960
tataatgaga gaaattag                                                    978
```

```
<210> SEQ ID NO 7
<211> LENGTH: 978
<212> TYPE: DNA
<213> ORGANISM: Artificial Sequence
<220> FEATURE:
<223> OTHER INFORMATION: Synthesized

<400> SEQUENCE: 7
atggccagta tggataaggt ttttgcaggc tatgctgccc gtcaagcaat cttagaaagt       60
accgaaacta cgaacccgtt tgccaaagga attgcctggg tcgaagggga actcgttcct      120
ttagctgaag cacgcattcc actcctcgat cagggcttca tgcactccga tctgacctac      180
gacgtaccgt ctgtttggga tgggcgattt tttcgtttag atgatcatct tacacgcctg      240
gaagcaagct gcaccaagct gaggctgcgt ctacccttac cacgtgatga agttaaacaa      300
atcctggtgg aaatggtcgc aaaatctggt attcgggatg cattagttga aacgatagtc      360
acccgcggtc ttaaaggggt gcgaggaact cgtccggaag atatagtgaa caacctgtac      420
atgtttgtgc agccgtacgt gtgggttatg gagccggata tgcagcgcgt aggcggcagc      480
gcagtggtgg ctaggaccgt ccgccgggta ccaccgggcg ctattgatcc gaccgtcaag      540
aatcttcagt ggggtgatct tgttcgtgga atgtttgaag cggctgatcg tggcgcaaca      600
tatcccttcc ttaccgacgg cgatgcgcac ctgactgaag gatcgggttt taatatagta      660
ttagtcaaag ctggcgtcct gtatacgcca gatcgcgggg tgctgcaggg agtgactcgc      720
aagtccgtta tcaacgctgc tgaagccttt ggaatagcag tgcgggttga gttcgttcca      780
gttgagctgg cctaccggtg tgacgagatt ttcatgtgca cgacggcggg tggcattatg      840
cctatcacaa cattggacgg tatgcctgta aatgatgggc aaattgggcc tattacgaaa      900
aaaatatggg acggttattg ggcgatgcat tatgacgccg cgtattcgtt cgagatcgac      960
tataatgaga gaaattag                                                    978
```

```
<210> SEQ ID NO 8
```

```
<211> LENGTH: 978
<212> TYPE: DNA
<213> ORGANISM: Artificial Sequence
<220> FEATURE:
<223> OTHER INFORMATION: Synthesized

<400> SEQUENCE: 8
atggccagta tggataaggt ttttgcaggc tatgctgccc gtcaagcaat cttagaaagt      60
accgaaacta cgaacccgtt tgccaaagga attgcctggg tcgaagggga actcgttcct     120
ttagctgaag cacgcattcc actcctcgat cagggcttca tgcactccga tctgacctac     180
gacgtaccgt ctgtttggga tgggcgattt tttcgtttag atgatcatct tacacgcctg     240
gaagcaagct gcaccaagct gaggctgcgt ctacccttac cacgtgatca agttaaacaa     300
atcctggtgg aaatggtcgc aaaatctggt attcgggatg catttgttga attgatagtc     360
acccgcggtc ttaaaggggt gcgaggaact cgtccggcag atatagtgaa caacctgtac     420
atgtttgtgc agccgtacgt gtgggttatg gagccggata tgcagcgcgt aggcggcagc     480
gcagtggtgg ctaggaccgt ccgccgggta ccaccgggcg ctattgatcc gaccgtcaag     540
aatcttcagt ggggtgatct tgttcgtgga atgtttgaag cggctgatcg tggcgcaaca     600
tatcccttcc ttaccgacgg cgatgcgcac ctgactgaag gatcgggttt taatatagta     660
ttagtcaaag atggcgtcct gtatacgcca gatcgcgggg tgctgcaggg agtgactcgc     720
aagtccgtta tcgacgctgc tgaagccttt ggaatagaag tgcgggttga gttcgttcca     780
gttgagctgg cctaccggtg tgacgagatt ttcatgtgca cgacggcggg tggcattatg     840
cctatcacaa cattggacgg tatgcctgta aatgatgggc aaattgggcc tattacgaaa     900
aaaatatggg acggttattg ggcgatgcat tatgacgccg cgtattcgtt cgagatcgac     960
tataatgaga gaaattag                                                  978

<210> SEQ ID NO 9
<211> LENGTH: 978
<212> TYPE: DNA
<213> ORGANISM: Artificial Sequence
<220> FEATURE:
<223> OTHER INFORMATION: Synthesized

<400> SEQUENCE: 9
atggccagta tggataaggt ttttgcaggc tatgctgccc gtcaagcaat cttagaaagt      60
accgaaacta cgaacccgtt tgccaaagga attgcctggg tcgaagggga actcgttcct     120
ttagctgaag cacgcattcc actcctcgat cagggcttca tgcactccga tctgacctac     180
gacgtaccgt ctgtttggga tgggcgattt tttcgtttag atgatcatat tacacgcctg     240
gaagcaagct gcaccaagct gaggctgcgt ctacccttac cacgtgatca agttaaacaa     300
atcctggtgg aaatggtcgc aaaatctggt attcgggatg catttgttga attgatagtc     360
acccgcggtc ttaaaggggt gcgaggaact cgtccgcgtg atatagtgaa caacctgtac     420
atgtttgtgc agccgtacgt gtgggttatg gagccggata tgcagcgcgt aggcggcagc     480
gcagtggtgg ctaggaccgt ccgccgggta ccaccgggcg ctattgatcc gaccgtcaag     540
aatcttcagt ggggtgatct tgttcgtgga atgtttgaag cggctgatcg tggcgcaaca     600
tatcccttcc ttaccgacgg cgatgcgaac ctgactgaag gatcgggttt taatatagta     660
ttagtcaaag atggcgtcct gtatacgcca gatcgcgggg tgctgcaggg agtgactcgc     720
aagtccgtta tcgacgctgc tgaagccttt ggaatagaag tgcgggttga gttcgttcca     780
gttgagctgg cctaccggtg tgacgagatt ttcatgtgca cgacggcggg tggcattatg     840
```

```
cctatcacaa cattggacgg tatgcctgta aatgatgggc aaattgggcc tattacgaaa    900
aaaatatggg acggttattg ggcgatgcat tatgacgccg cgtattcgtt cgagatcgac    960
tataatgaga gaaattag                                                  978
```

```
<210> SEQ ID NO 10
<211> LENGTH: 51
<212> TYPE: DNA
<213> ORGANISM: Artificial Sequence
<220> FEATURE:
<223> OTHER INFORMATION: Synthesized

<400> SEQUENCE: 10
atggccagta tggataaggt ttttgcaggc tatgctgccc gtcaagcaat c             51
```

```
<210> SEQ ID NO 11
<211> LENGTH: 60
<212> TYPE: DNA
<213> ORGANISM: Artificial Sequence
<220> FEATURE:
<223> OTHER INFORMATION: Synthesized

<400> SEQUENCE: 11
cccgtttgcc aaaggaattg cctgggtcga aggggaactc gttcctttag ctgaagcacg    60
```

```
<210> SEQ ID NO 12
<211> LENGTH: 60
<212> TYPE: DNA
<213> ORGANISM: Artificial Sequence
<220> FEATURE:
<223> OTHER INFORMATION: Synthesized

<400> SEQUENCE: 12
gcttcatgca ctccgatctg acctacgacg taccgtctgt ttgggatggg cgattttttc    60
```

```
<210> SEQ ID NO 13
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (51)..(51)
<223> OTHER INFORMATION: n is c or g

<400> SEQUENCE: 13
tggaagcaag ctgcaccaag ctgaggctgc gtctaccctt accacgtgat naagttaaac    60
```

```
<210> SEQ ID NO 14
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(23)
<223> OTHER INFORMATION: n is a, t, c, g or u

<400> SEQUENCE: 14
aatctggtat tcgggatgca ttngttgaat tgatagtcac ccgcggtctt aaaggggtgc    60
```

```
<210> SEQ ID NO 15
<211> LENGTH: 60
<212> TYPE: DNA
```

```
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(23)
<223> OTHER INFORMATION: n is a, t, c, g or u

<400> SEQUENCE: 15
aatctggtat tcgggatgca ttngttgaaa cgatagtcac ccgcggtctt aaagggggtgc    60

<210> SEQ ID NO 16
<211> LENGTH: 60
<212> TYPE: DNA
<213> ORGANISM: Artificial Sequence
<220> FEATURE:
<223> OTHER INFORMATION: Synthesized

<400> SEQUENCE: 16
tagtgaacaa cctgtacatg tttgtgcagc cgtacgtgtg ggttatggag ccggatatgc    60

<210> SEQ ID NO 17
<211> LENGTH: 60
<212> TYPE: DNA
<213> ORGANISM: Artificial Sequence
<220> FEATURE:
<223> OTHER INFORMATION: Synthesized

<400> SEQUENCE: 17
tagtgaacaa cctgtacatg tttgtgcagc cgtacgtgtg ggtttgcgag ccggatatgc    60

<210> SEQ ID NO 18
<211> LENGTH: 60
<212> TYPE: DNA
<213> ORGANISM: Artificial Sequence
<220> FEATURE:
<223> OTHER INFORMATION: Synthesized

<400> SEQUENCE: 18
tggtggctag gaccgtccgc cgggtaccac cgggcgctat tgatccgacc gtcaagaatc    60

<210> SEQ ID NO 19
<211> LENGTH: 60
<212> TYPE: DNA
<213> ORGANISM: Artificial Sequence
<220> FEATURE:
<223> OTHER INFORMATION: Synthesized

<400> SEQUENCE: 19
tgttcgtgga atgtttgaag cggctgatcg tggcgcaaca tatcccttcc ttaccgacgg    60

<210> SEQ ID NO 20
<211> LENGTH: 60
<212> TYPE: DNA
<213> ORGANISM: Artificial Sequence
<220> FEATURE:
<223> OTHER INFORMATION: Synthesized

<400> SEQUENCE: 20
gatcgggttt taatatagta ttagtcaaag atggcgtcct gtatacgcca gatcgcgggg    60

<210> SEQ ID NO 21
<211> LENGTH: 60
<212> TYPE: DNA
<213> ORGANISM: Artificial Sequence
<220> FEATURE:
<223> OTHER INFORMATION: Synthesized
```

```
<220> FEATURE:
<221> NAME/KEY: variation
<222> LOCATION: (12)..(12)
<223> OTHER INFORMATION: r is a or g
<220> FEATURE:
<221> NAME/KEY: variation
<222> LOCATION: (37)..(37)
<223> OTHER INFORMATION: m is a or c

<400> SEQUENCE: 21
agtccgttat cracgctgct gaagcctttg gaatagmagt gcgggttgag ttcgttccag    60

<210> SEQ ID NO 22
<211> LENGTH: 60
<212> TYPE: DNA
<213> ORGANISM: Artificial Sequence
<220> FEATURE:
<223> OTHER INFORMATION: Synthesized

<400> SEQUENCE: 22
tgacgagatt ttcatgtgca cgacggcggg tggcattatg cctatcacaa cattggacgg    60

<210> SEQ ID NO 23
<211> LENGTH: 60
<212> TYPE: DNA
<213> ORGANISM: Artificial Sequence
<220> FEATURE:
<223> OTHER INFORMATION: Synthesized

<400> SEQUENCE: 23
tgacgagatt ttcatgtgca cgacggcggg tggcatttgc cctatcacaa cattggacgg    60

<210> SEQ ID NO 24
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (3)..(3)
<223> OTHER INFORMATION: r is a or g

<400> SEQUENCE: 24
aarttgggcc tattacgaaa aaaatatggg acggttattg ggcgatgcat tatgacgccg    60

<210> SEQ ID NO 25
<211> LENGTH: 60
<212> TYPE: DNA
<213> ORGANISM: Artificial Sequence
<220> FEATURE:
<223> OTHER INFORMATION: Synthesized

<400> SEQUENCE: 25
caattccttt ggcaaacggg ttcgtagttt cggtactttc taagattgct tgacgggcag    60

<210> SEQ ID NO 26
<211> LENGTH: 60
<212> TYPE: DNA
<213> ORGANISM: Artificial Sequence
<220> FEATURE:
<223> OTHER INFORMATION: Synthesized

<400> SEQUENCE: 26
cagatcggag tgcatgaagc cctgatcgag gagtggaatg cgtgcttcag ctaaaggaac    60

<210> SEQ ID NO 27
```

```
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (26)..(26)
<223> OTHER INFORMATION: k is g or t

<400> SEQUENCE: 27
gtgcagcttg cttccaggcg tgtaakatga tcatctaaac gaaaaaatcg cccatcccaa    60

<210> SEQ ID NO 28
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (52)..(52)
<223> OTHER INFORMATION: s is c or g

<400> SEQUENCE: 28
catcccgaat accagatttt gcgaccattt ccaccaggat ttgtttaact tsatcacgtg    60

<210> SEQ ID NO 29
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (26)..(26)
<223> OTHER INFORMATION: k is g or t

<400> SEQUENCE: 29
catgtacagg ttgttcacta tatctkccgg acgagttcct cgcacccctt taagaccgcg    60

<210> SEQ ID NO 30
<211> LENGTH: 60
<212> TYPE: DNA
<213> ORGANISM: Artificial Sequence
<220> FEATURE:
<223> OTHER INFORMATION: Synthesized

<400> SEQUENCE: 30
gcggacggtc ctagccacca ctgcgctgcc gcctacgcgc tgcatatccg gctccataac    60

<210> SEQ ID NO 31
<211> LENGTH: 60
<212> TYPE: DNA
<213> ORGANISM: Artificial Sequence
<220> FEATURE:
<223> OTHER INFORMATION: Synthesized

<400> SEQUENCE: 31
gcggacggtc ctagccacca ctgcgctgcc gcctacgcgc tgcatatccg gctcgcaaac    60

<210> SEQ ID NO 32
<211> LENGTH: 60
<212> TYPE: DNA
<213> ORGANISM: Artificial Sequence
<220> FEATURE:
<223> OTHER INFORMATION: Synthesized

<400> SEQUENCE: 32
```
cttcaaacat tccacgaaca agatcacccc actgaagatt cttgacggtc ggatcaatag    60

<210> SEQ ID NO 33
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (33)..(33)
<223> OTHER INFORMATION: k is g or t

<400> SEQUENCE: 33
tactatatta aaacccgatc cttcagtcag gtkcgcatcg ccgtcggtaa ggaagggata    60

<210> SEQ ID NO 34
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (8)..(8)
<223> OTHER INFORMATION: y is c or t

<400> SEQUENCE: 34
gcagcgtyga taacggactt gcgagtcact ccctgcagca ccccgcgatc tggcgtatac    60

<210> SEQ ID NO 35
<211> LENGTH: 60
<212> TYPE: DNA
<213> ORGANISM: Artificial Sequence
<220> FEATURE:
<223> OTHER INFORMATION: Synthesized

<400> SEQUENCE: 35
gcacatgaaa atctcgtcac accggtaggc cagctcaact ggaacgaact caacccgcac    60

<210> SEQ ID NO 36
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: variation
<222> LOCATION: (18)..(18)
<223> OTHER INFORMATION: y is c or t
<220> FEATURE:
<221> NAME/KEY: variation
<222> LOCATION: (26)..(26)
<223> OTHER INFORMATION: y is c or t

<400> SEQUENCE: 36
tttcgtaata ggcccaaytt gcccaycatt tacaggcata ccgtccaatg ttgtgatagg    60

<210> SEQ ID NO 37
<211> LENGTH: 51
<212> TYPE: DNA
<213> ORGANISM: Artificial Sequence
<220> FEATURE:
<223> OTHER INFORMATION: Synthesized

<400> SEQUENCE: 37
ctaatttctc tcattatagt cgatctcgaa cgaatacgcg gcgtcataat g    51

```
<210> SEQ ID NO 38
<211> LENGTH: 66
<212> TYPE: DNA
<213> ORGANISM: Artificial Sequence
<220> FEATURE:
<223> OTHER INFORMATION: Synthesized

<400> SEQUENCE: 38
ggctagcatg actggtggac atgcaccacc accaccacca catggccagt atggataagg      60
tttttg                                                                 66

<210> SEQ ID NO 39
<211> LENGTH: 51
<212> TYPE: DNA
<213> ORGANISM: Artificial Sequence
<220> FEATURE:
<223> OTHER INFORMATION: Synthesized

<400> SEQUENCE: 39
gagtgcggcc gcaagcttgt ctaatttctc tcattatagt cgatctcgaa c               51

<210> SEQ ID NO 40
<211> LENGTH: 18
<212> TYPE: DNA
<213> ORGANISM: Artificial Sequence
<220> FEATURE:
<223> OTHER INFORMATION: Synthesized

<400> SEQUENCE: 40
acaagcttgc ggccgcac                                                    18

<210> SEQ ID NO 41
<211> LENGTH: 25
<212> TYPE: DNA
<213> ORGANISM: Artificial Sequence
<220> FEATURE:
<223> OTHER INFORMATION: Synthesized

<400> SEQUENCE: 41
gtccaccagt catgctagcc atatg                                            25
```

ω-TRANSAMINASE MUTANT OBTAINED BY DNA SYNTHETIC SHUFFLING COMBINED MUTATION AND USE

This application claims priority to Chinese Patent Applications No. 2020114150071 filed Dec. 4, 2020, which is hereby incorporated by reference.

FIELD OF TECHNOLOGY

The present invention relates to the field of biological technologies, particularly to a ω-transaminase mutant obtained by DNA synthetic shuffling combined mutation and use thereof.

BACKGROUND TECHNOLOGY

Chiral amine is a key intermediate or chiral building block for synthesis of many important drugs. At present, a main production method of these important chiral amine compounds is a chemical synthesis method, and generally needs expensive transition metal complex catalysts such as ruthenium and rhodium or extreme reaction conditions such as high pressure, and meanwhile has inherent drawbacks such as poor selectivity, low yield and many discharging. Therefore, whether chiral amines can be industrially produced through an asymmetrical biological catalysis method has become the focus of researchers. Enzyme-catalyzed asymmetric synthesis of chiral amine compounds mainly uses two enzymes, wherein one enzyme is amino dehydrogenase and the other enzyme is ω-transaminase. Use of amino dehydrogenase is required to use a corresponding coenzyme regeneration system. And the ω-transaminase depends on coenzyme pyridoxal phosphate (PLP) to reversely catalyze the transfer of amino groups to prochiral ketones to prepare chiral amine compounds, and has become an important biological catalyst for preparing optical pure chiral amines due to high stereo selectivity and mild reaction conditions.

The catalytic process of ω-transaminase is composed of two half-transamination reactions and follows a double-substrate ping-pong mechanism. As shown in FIG. 1, in the first half reaction, an amino donor substrate and a coenzyme form a Schiff base (aldimine). After further gain and loss of protons and transfer of amino to the coenzyme, 5'-pyridoxamine phosphate (PMP) ligated with ketonic acid and an enzyme is obtained. In the second half reaction, the amino is transferred from PMP to a receptor to obtain PLP and produce chiral amines.

The ω-transaminase from *Aspergillus terreus* uses ketone compounds as raw materials to efficiently produce chiral amines through stereoselective transamination. Studies have shown that the wild-type enzyme has a half-life period of only 6.9 min at 40° C., and its thermal stability needs to be further improved. For example, Chinese patents CN105441404A and CN105950581A disclose that a wild-type ω-transaminase is modified by using a site-directed mutagenesis technology to obtain a ω-transaminase mutant with further improved thermal stability, so that the ω-transaminase mutant is more suitable for industrial application.

At present, a directed evolution technology of enzymes is a method in which a spatial structure and a catalytic mechanism of enzymes are not known in advance, special evolution conditions are artificially created, a natural evolution mechanism is simulated, enzyme genes are modified in vitro, and enzymes with more excellent required performance are directionally selected or screened, or new enzymes that do not exist in nature and has a good property are created. In recent years, with the establishment and development of the directed evolution technology, there are more and more studies for improving the stability of enzymes through this technology. These studies mainly include irrational design, rational design and semi-rational design. With the deepening of related researches, researches on molecular modification of a transaminase using a semi-rational design strategy have attracted much attention.

The inventors of the present invention have been conducting research directed at catalytic synthesis of chiral amines through the transaminase. The transaminase is modified by a semi-rational design method, including addition of a disulfide bond (semi-rational design based on a structure), sequence identity (semi-rational design based on a sequence) and constructing a co-evolution network to modify the thermal stability of the transaminase and obtain a certain improvement. However, various methods to improve the thermal stability of the transaminase have their own advantages and disadvantages. Although the mutant obtained in the above experiment can increase the half-inactivation temperature and prolong the half-life period compared with the wild-type ω-transaminase, the half-inactivation temperature and the half-life period of the above mutant still need to be further improved if it is to be better applied in practical production.

SUMMARY OF THE INVENTION

The present invention is a method based on DNA synthetic shuffling. An *Aspergillus terreus* ω-transaminase mutant having further improved enzyme activity and thermal stability is obtained by this method.

According to the present invention, a screening efficiency and a screening quantity are greatly improved by combining solid plate screening with 96-well plate screening.

The present invention provides a ω-transaminase mutant obtained by DNA synthetic shuffling combined mutation, wherein the ω-transaminase mutant is obtained by DNA synthetic shuffling of a wild type ω-transaminase from *Aspergillus terrus*, the amino acid sequence of the wild type ω-transaminase is shown in SEQ ID NO:1, and the mutation site of the ω-transaminase mutant is any one of: (1) F115L-H210N-M150C-M280C; (2) F115L-H210N; (3) F115L-H210N-E253A-I295V; (4) I77L-F115L-E133A-H210N-N245D; (5) I77L-Q97E-F115L-L118T-E253A-G292D; (6) I77L-E133A-N245D-G292D; and (7) H210N-N245D-E253A-G292D. The mutation sites of the above mutant are mutation forms of multiple sites, for example (1) F115L-H210N-M150C-M280C represents that an amino acid at position 115 is mutated from phenylalanine to leucine, an amino acid at position 210 is mutated from histidine to asparaginate, an amino acid at position 150 is mutated from methionine to cysteine and an amino acid at position 280 is mutated from methionine to cysteine, the half-inactivation temperature of the mutant is 52.2° C. which is increased by 13.7° C. compared with that of the wild type ω-transaminase, and the half-life period of the mutant at 40° C. is 172.7 min which is prolonged by 165.8 min compared with that of the wild type ω-transaminase. The nucleotide acid sequence of the wild type ω-transaminase gene is shown in SEQ ID NO: 2.

The present invention also discloses use of the ω-transaminase mutant in catalyzing (R)-(+)-α-methylbenzylamine to produce acetophenone.

The present invention also discloses a gene encoding the ω-transaminase mutant. Preferably, the nucleotide acid sequences of the gene are shown in SEQ ID NOs: 3-9. The nucleotide acid sequence of the mutant F115L-H210N-M150C-M280C is shown in SEQ ID NO: 3; the nucleotide acid sequence of the mutant F115L-H210N is shown in SEQ ID NO: 4; the nucleotide acid sequence of the mutant F115L-H210N-E253A-I295V is shown in SEQ ID NO: 5; the nucleotide acid sequence of the mutant I77L-F115L-E133A-H210N-N245D is shown in SEQ ID NO: 6; the nucleotide acid sequence of the mutant I77L-Q97E-F115L-L118T-E253A-G292D is shown in SEQ ID NO: 7; the nucleotide acid sequence of the mutant I77L-E133A-N245D-G292D is shown in SEQ ID NO: 8; and the nucleotide acid sequence of the mutant H210N-N245D-E253A-G292D is shown in SEQ ID NO: 9.

The present invention also discloses use of the gene in catalyzing (R)-(+)-α-methylbenzylamine to produce acetophenone.

The present invention also discloses a recombinant expression vector containing the gene.

The present invention also discloses a genetically engineered bacterium containing the recombinant expression plasmid.

The present invention also discloses use of the genetically engineered bacterium in catalyzing (R)-(+)-α-methylbenzylamine to produce acetophenone.

Compared with the prior art, the present invention has the following beneficial effects: (1) the ω-transaminase mutant of the present invention is obtained by mutating phenylalanine at position 115, methionine at position 150, histidine at position 210 and methionine at position 280 of the *Aspergillus terreus* ω-transaminase to leucine, cysteine, asparagine and cysteine respectively, the half-inactivation temperature ($T_{50}^{10}$) of the ω-transaminase mutant is 52.2±0.42° C. which is improved by 13.7° C. compared with that of the wild type, the half-life period ($t_{1/2}$) at 40° C. is 172.7±3.68 min which is 25 times as that of the wild type, and the thermal stability is significantly improved; (2) according to the present invention, forward mutations obtained in the previous stage are randomly combined through the DNA synthetic shuffling combined mutation method, it is verified through experiments that this method can effectively improve the probability of forward mutation and increase experimental efficiency and feasibility, and is capable of obtaining mutant enzymes with thermodynamic stability remarkably superior to that of wild enzymes via screening.

DETAILED DESCRIPTION OF THE EMBODIMENTS

Example 1

Figure 1:
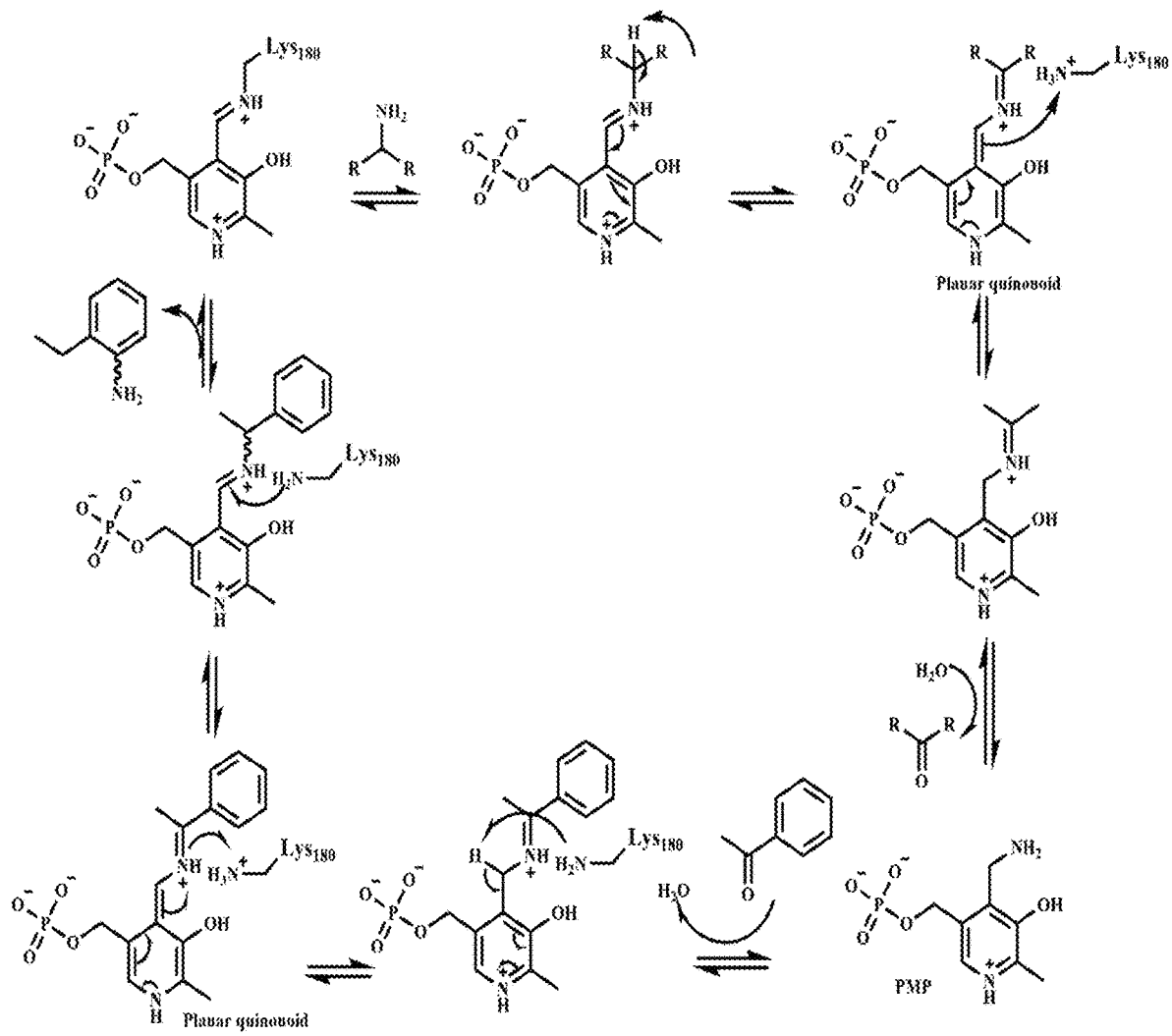
FIG. 1 is a diagram of a catalytic process in which a ω-transaminase depends on coenzyme pyridoxal phosphate (PLP) to reversely catalyze the transfer of amino groups to prochiral ketones to prepare chiral amine compounds.
Figure 2:
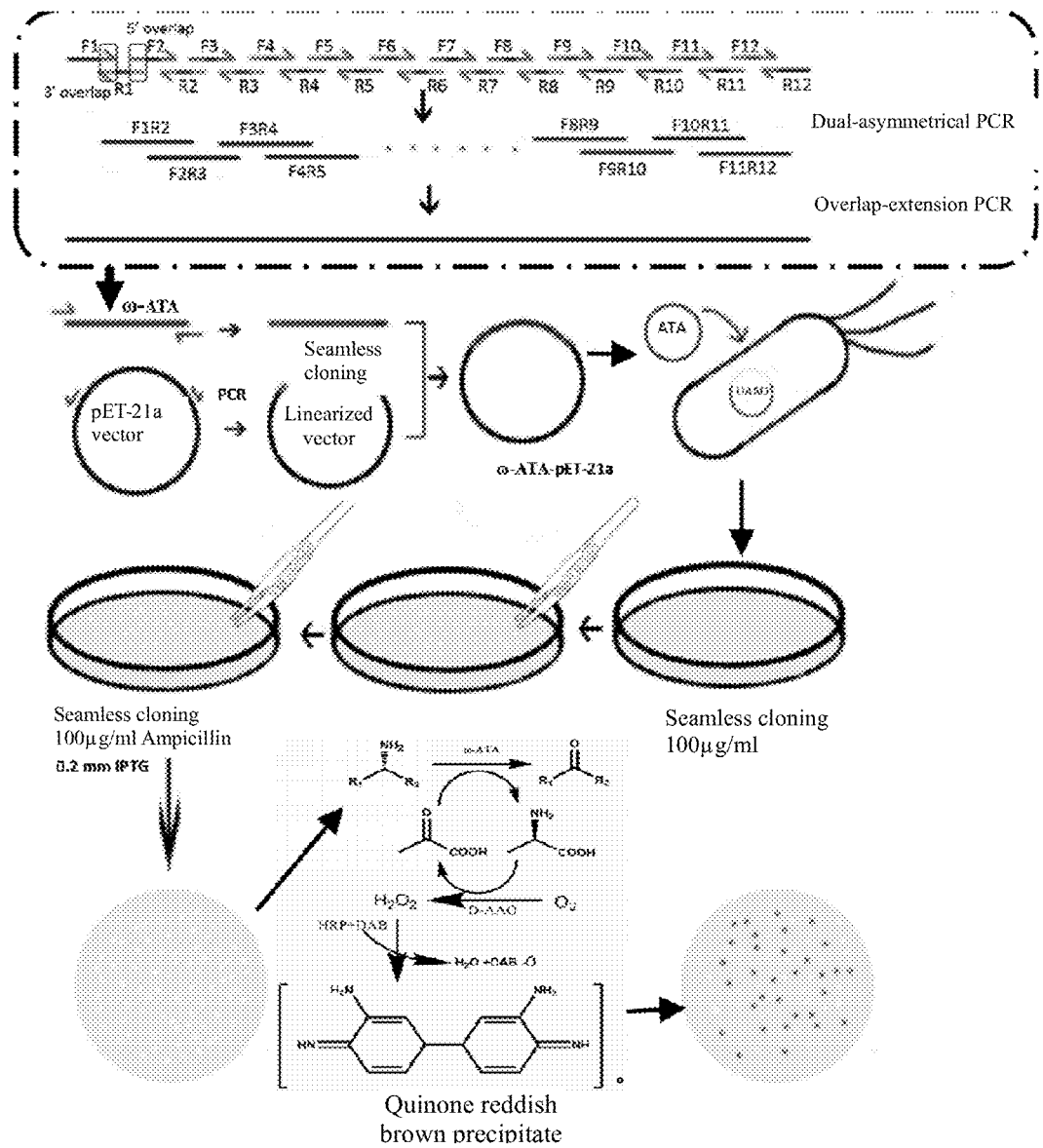
FIG. 2 is a flowchart of DNA synthetic shuffling combined mutation and solid plate screening.

1. Experimental Materials
  (1) LB culture medium: 10 g/L tryptone (available from Oxoid), 5 g/L yeast powder (available from Oxoid), 10 g/L sodium chloride (available from Shenggong Bioengineering Co., Ltd. (Shanghai)), and pH 7.0. LB solid culture medium: 2% (mass percent) agar powder was added into an LB liquid culture medium.

Sodium chloride, glycerol, calcium chloride, imidazole, glacial acetic acid, disodium hydrogen phosphate, sodium dihydrogen phosphate, 5-pyridoxal phosphate, a Coomassie brilliant blue protein concentration determination kit, a Ni-NTA chromatography medium, isopropyl-β-D-thiogalactoside (IPTG), kanamycin sulfate, horseradish peroxidase, ampicillin, DNA and protein Marker were available from Shenggong Bioengineering Co., Ltd. (Shanghai). In the present invention, the ω-transaminase gene (ω-TA gene) optimized by codons was entrusted to Universal Biosystems (Anhui) Co., Ltd. for full gene synthesis, and the pET-21a plasmid was used as a cloning vector in the gene synthesis service.

(2) Dimethyl sulfoxide (DMSO), pyruvic acid, (R)-(+)-α-methylbenzylamine, 3,3-diaminobenzidine tetrahydrochloride hydrate (DAB) were available from Aladdin Biochemical Technology Co., Ltd. The PrimeSTAR Max DNA polymerase was available from TaKaRa Company; a nucleic acid transfer membrane (imprinting membrane) was available from GE Healthcare Company, and DpnI was available from Thermo Scientific Company.

(3) Formula of buffer:
  20 mmol/L elution buffer: 50 mmol/L sodium dihydrogen phosphate, 300 mmol/L sodium chloride, 20 mmol/L imidazole, and pH 8.0; 50 mmol/L elution buffer: 50 mmol/L sodium dihydrogen phosphate, 300 mmol/L sodium chloride, 50 mmol/L imidazole, and pH 8.0; 100 mmol/L elution buffer: 50 mmol/L sodium dihydrogen phosphate, 300 mmol/L sodium chloride, 100 mmol/L imidazole, and pH 8.0; 250 mmol/L elution buffer: 50 mmol/L sodium dihydrogen phosphate, 300 mmol/L sodium chloride, 250 mmol/L imidazole, and pH 8.0.

Gel dyeing solution: 45.4 mL of methanol, 9.2 mL of glacial acetic acid and 0.05 g of Coomassie brilliant blue R250 were dissolved into 100 mL of deionized water; gel decolorizing solution: 5 mL of methanol and 7.5 mL of glacial acetic acid were dissolved into 100 mL of deionized water; electrophoretic buffer: 3.03 g of Tris, 14.4 g of glycine and 1 g of SDS were metered with deionized water until a constant volume of 1 L was reached, suction filtration was conducted with 0.22 μm filter paper, and refrigeration was performed at 4° C.

2. Combined Mutation
  Forward mutations obtained in the previous stage were randomly combined through DNA synthetic shuffling by using a combined mutation method so as to further improve the thermal stability of transaminase. Oligonucleotide primers for creating a combinatorial gene library are based on a method described by Ness, etc., and allow any required mutations by using degenerate codons, wherein the degenerate base S represents G/C, N represents A/T/C/G, R represents A/G, M represents A/C, K represents G/T, and Y represents C/T.

TABLE 1

Combined mutation primers and sequences thereof

| Primer name | Sequence 5'-3' |
|---|---|
| F1 (SEQ ID NO: 10) | ATGGCCAGTATGGATAAGGTTTTTGCAGGCTAT GCTGCCCGTCAAGCAATC |
| F2 (SEQ ID NO: 11) | CCCGTTTGCCAAAGGAATTGCCTGGGTCGAAGG GGAACTCGTTCCTTTAGCTGAAGCACG |
| F3 (SEQ ID NO: 12) | GCTTCATGCACTCCGATCTGACCTACGACGTAC CGTCTGTTTGGGATGGGCGATTTTTC |
| F4 (SEQ ID NO: 13) | TGGAAGCAAGCTGCACCAAGCTGAGGCTGCGTC TACCCTTACCACGTGATSAAGTTAAAC |
| F5 (SEQ ID NO: 14) | AATCTGGTATTCGGGATGCATTNGTTGAATTGA TAGTCACCCGCGGTCTTAAAGGGGTGC |
| F5-a (SEQ ID NO: 15) | AATCTGGTATTCGGGATGCATTNGTTGAAACGA TAGTCACCCGCGGTCTTAAAGGGGTGC |
| F6 (SEQ ID NO: 16) | TAGTGAACAACCTGTACATGTTTGTGCAGCCGT ACGTGTGGGTTATGGAGCCGGATATGC |
| F6-a (SEQ ID NO: 17) | TAGTGAACAACCTGTACATGTTTGTGCAGCCGT ACGTGTGGGTTTGCGAGCCGGATATGC |
| F7 (SEQ ID NO: 18) | TGGTGGCTAGGACCGTCCGCCGGGTACCACCGG GCGCTATTGATCCGACCGTCAAGAATC |
| F8 (SEQ ID NO: 19) | TGTTCGTGGAATGTTTGAAGCGGCTGATCGTGG CGCAACATATCCCTTCCTTACCGACGG |
| F9 (SEQ ID NO: 20) | GATCGGGTTTTAATATAGTATTAGTCAAAGATG GCGTCCTGTATACGCCAGATCGCGGGG |
| F10 (SEQ ID NO: 21) | AGTCCGTTATCRACGCTGCTGAAGCCTTTGGAA TAGMAGTGCGGGTTGAGTTCGTTCCAG |
| F11 (SEQ ID NO: 22) | TGACGAGATTTTCATGTGCACGACGGCGGGTGG CATTATGCCTATCACAACATTGGACGG |
| F11-a (SEQ ID NO: 23) | TGACGAGATTTTCATGTGCACGACGGCGGGTGG CATTTGCCCTATCACAACATTGGACGG |
| F12 (SEQ ID NO: 24) | AARTTGGGCCTATTACGAAAAAAATATGGACG GTTATTGGGCGATGCATTATGACGCCG |
| R1 (SEQ ID NO: 25) | CAATTCCTTTGGCAAACGGGTTCGTAGTTTCGG TACTTTCTAAGATTGCTTGACGGGCAG |
| R2 (SEQ ID NO: 26) | CAGATCGGAGTGCATGAAGCCCTGATCGAGGAG TGGAATGCGTGCTTCAGCTAAAGGAAC |
| R3 (SEQ ID NO: 27) | GTGCAGCTTGCTTCCAGGCGTGTAAKATGATCA TCTAAACGAAAAAATCGCCCATCCCAA |
| R4 (SEQ ID NO: 28) | CATCCCGAATACCAGATTTTGCGACCATTTCCA CCAGGATTTGTTTAACTTSATCACGTG |
| R5 (SEQ ID NO: 29) | CATGTACAGGTTGTTCACTATATCTKCCGGACG AGTTCCTCGCACCCCTTTAAGACCGCG |
| R6 (SEQ ID NO: 30) | GCGGACGGTCCTAGCCACCACTGCGCTGCCGCC TACGCGCTGCATATCCGGCTCCATAAC |
| R6-a (SEQ ID NO: 31) | GCGGACGGTCCTAGCCACCACTGCGCTGCCGCC TACGCGCTGCATATCCGGCTCGCAAAC |
| R7 (SEQ ID NO: 32) | CTTCAAACATTCCACGAACAAGATCACCCCACT GAAGATTCTTGACGGTCGGATCAATAG |
| R8 (SEQ ID NO: 33) | TACTATATTAAAACCCGATCCTTCAGTCAGGTK CGCATCGCCGTCGGTAAGGAAGGGATA |
| R9 (SEQ ID NO: 34) | GCAGCGTYGATAACGGACTTGCGAGTCACTCCC TGCAGCACCCCGCGATCTGGCGTATAC |
| R10 (SEQ ID NO: 35) | GCACATGAAAATCTCGTCACACCGGTAGGCCAG CTCAACTGGAACGAACTCAACCCGCAC |
| R11 (SEQ ID NO: 36) | TTTCGTAATAGGCCCAAYTTGCCCAYCATTTAC AGGCATACCGTCCAATGTTGTGATAGG |
| R12 (SEQ ID NO: 37) | CTAATTTCTCTCATTATAGTCGATCTCGAACGA ATACGCGGCGTCATAATG |
| ATA-F (SEQ ID NO: 38) | GGCTAGCATGACTGGTGGACATGCACCACCACC ACCACCACATGGCCAGTATGGATAAGGTTTTTG |
| ATA-R (SEQ ID NO: 39) | GAGTGCGGCCGCAAGCTTGTCTAATTTCTCTCA TTATAGTCGATCTCGAAC |
| PET-21a-F (SEQ ID NO: 40) | ACAAGCTTGCGGCCGCAC |
| PET-21a-R (SEQ ID NO: 41) | GTCCACCAGTCATGCTAGCCATATG |

Notes: the underline represents a mutation site, a primer name with F represents an upstream primer, and a primer name with R represents a downstream primer.

The mutation library and complete target gene fragments were obtained by three-step independent PCR (two-step assembling PCR and one-step amplification PCR), then connecting PCR products with a pET-21a vector through primer seamless cloning and transferring the connected product into competent *Escherichia coli* BL21(DE3) (containing pRST-DAAO plasmids)

(1) The first-step PCR used primers (F1-R12) in Table 1, each group of PCR used four adjacent oligonucleotide primers (two forward primers and two reverse primers), a PCR amplification system: 25 μL of PrimeSTAR Max Premix 2×; 0.4 μL of inner primer (10 μM), 2 μL of outer primer (10 μM), and ultrapure water sterilized at high temperature was supplemented so that a total volume was 50 μL. PCR amplification conditions: denature for 20 seconds at 98° C., anneal for 15 seconds at 55° C., extend for 30 seconds at 72° C., and 30 cycles. 5 μL of PCR product was evenly mixed with loading buffer and then tested via 1% agarose gel electrophoresis, and then 5 μL of each of 11 groups of PCR products obtained was taken respectively and mixed, and then purified through a PCR product purification kit.

(2) There were about 60 bp of overlaps between every adjacent two groups of PCR products in the first step, and PCR in the second step was to assemble the mixed fragments into a complete target gene. A 50 μL PCR amplification system contained 10 μL of purified PCR product mixture, 25 μL of PrimeSTAR Max Premix 2× and 15 μL of ultrapure water sterilized at high temperature. PCR amplification conditions: denature for 30 seconds at 94° C., extend for 120 seconds at 68° C., and 20 cycles. The PCR product was purified by a purification kit.

(3) After the assembling in the second step, primers were designed online so that there were about 15~20 bp of transaminases between the primers and the target genes and between the primers and the vectors, and the primers were further designed to add histidine tags at the N end of the protein. According to the primer ATA-F, ATA-R was subjected to third-step PCR, so as to increase the quantity of reassembled complete genes. PCR amplification system: 25 µL of PrimeSTAR Max Premix 2×; 2 µL of upstream primer (10 µM), 2 µL of downstream primer (10 µM), 1 µL of PCR product template (100 ng/µL), and ultrapure water sterilized at high temperature was added so that a total volume was 50 µL. PCR amplification conditions: denature for 1 min at 98° C.; denature for 20 seconds at 98° C., anneal for 15 seconds at 55° C., extend for 2 min at 72° C., and 30 cycles; extend for 7 min at 72° C. The PCR products were correctly detected by electrophoresis.

(4) pET-21a vector PCR: pET-21a-R was subjected to vector PCR using primer pET-21a-F so that the vector was linearized and there was a 15-'20 bp homologous arm between the vector and the target gene. PCR amplification system: 25 µL of PrimeSTAR Max Premix 2×; 2 µL of upstream primer (10 µM), 2 µL of downstream primer (10 µM), 1 µL of plasmid template (10 ng)/µL), and ultrapure water sterilized at high temperature was added so that a total volume was 50 µL. PCR amplification conditions: denature for 1 min at 98° C.; denature for 20 seconds at 98° C., anneal for 15 seconds at 55° C., extend for 2 min at 72° C., and 30 cycles; extend for 7 min at 72° C. PCR products were correctly detected by electrophoresis and recycled by a gel recycle kit. The methylated mother template in the obtained gel recycled product was identified by using Dpn I and degraded. Digestion reaction: 17 µL of PCR product, 2 µL of Buffer and 1 µL of Dpn I. Digest for 2 hours at 37° C.

(5) Homologous recombination: a target gene was ligated with a linearized vector. Cloning vector usage=[0.02× logarithm of cloning vector base]ng (0.03 pm), inserted fragment usage=[0.04×logarithm of cloning vector base]ng (0.03 pm). 10 µL of recombination reaction system was prepared on ice: 2 µL of pET-21a linearized vector (100 ng/µL), 2 µL of target gene fragment (40 ng/µL), 5 µL of ClonExpress Mix 2×, 1 µL of ddH$_2$O. Reconstitution conditions: ligate for 30 min at 50° C., decrease the temperature to 4° C., or immediately cool on ice.

The ligation product was transferred into *E. coli* BL 21 competent cells (containing pRSF DAAO plasmids) by using a heat shock method.

3. Preparation of Competent *Escherichia coli* BL21 (DE3) Containing Single Plasmid pRSF-DAAO (1) The fresh *Escherichia coli* single colonies were picked and inoculated into 5 mL of LB liquid culture medium and cultured overnight at 37° C. and 160 r/min until OD$_{600}$ was about 0.6-0.8.

(2) 2 mL of the above culture solution was inoculated into 200 mL of LB liquid culture medium in a ratio of 1% (v/v), and cultured for 2 h at 37° C. and 180 r/min until OD$_{600}$ was about 0.4.

(3) The culture solution was placed for 0.5 h in an ice-water bath, and centrifuged for 10 min at 4° C. and 4500 r/min to collect bacteria.

(4) The bacterial cells were re-suspended with 10 mL of pre-cooled 10 mM CaCl$_2$, placed for 15 min in ice-water bath, and centrifuged for 10 min at 4° C. and 4500 r/min to collect bacteria.

(5) Step (4) was repeated.

(6) 6 mL of pre-cooled 10 mM CaCl$_2$ solution (containing 15% glycerol) was added into the bacteria. The bacterial cells were re-suspended, placed for 3~5 min on ice, packaged into sterile EP tubes, and then stored in a −80° C. refrigerator.

4. Construction of Mutation Library

*E. coli* BL 21 competent cells (containing pRSF-DAAO plasmids) deposited at −80° C. were taken and thawed on ice, then a homologous recombinant ligation product solution (5~10 µL) was added, the above substances were gently and evenly shaken and then placed for 30 min on ice. The obtained mixture was subjected to heat shock for 90 seconds in water bath at 42° C., and then quickly placed on ice to be fully cooled for 3 min. 0.8 mL of LB liquid culture medium was into the tube to culture for 1 hour at 37° C. so that the bacteria were restored to be in a normal growth state, and kanamycin resistance and ampicillin resistance genes encoded by double plasmids were expressed. 100 µL of bacterial solution was taken and evenly coated on an LB plate (containing 50 µg/mL kanamycin and 100 µg/mL ampicillin) covered with a Hybond-N imprinting membrane, the front surface of the plate was placed upward for 0.5 hour. After the bacterial solution was completely absorbed by the culture medium, the plate was reversely placed, and the bacterial solution was cultured for 16 hours at 37° C. The membrane was imprinted on a motherboard so that the bacteria continued to grow for 12 hours at 37° C., and then stored in a 4° C. refrigerator. Then, the membrane was transferred to an LB plate containing 0.2 mm isopropyl-β-D-thiogalactoside (IPTG), 50 µg/mL kanamycin and 100 µg/mL ampicillin, and put in a 25° C. incubator to culture for 20 hours, and then the membrane was stored in −80° C. refrigerator.

The single colony was randomly picked from the above plate and inoculated into 5 mL of LB culture medium containing 50 µg/mL kanamycin and 100 µg/mL ampicillin, cultured for 3-4 hours at 37° C. and 200 r/min. 1-2 ul of bacterial solution was diluted by 100 volumes, and the bacterial solution was subjected to PCR for 10-15 min in boiling water bath to verify the existence of double plasmids. pET21a-ATA (Colony-F/R) and pRSF-DAAO (DAAO-F/R) plasmids were used as templates to design a primer colony PCR system as follows: 25 µL of PrimeSTAR Max Premix 2×; 1 µL of upstream primer (10 µM), 1 µL of downstream primer (10 µM), 2 µL of template, and ultrapure water sterilized at high temperature was supplemented so that a total volume was 50 µL. Electrophoresis detection was conducted with 1% agarose gel.

5. Primary Screening and Secondary Screening of Mutation Library

The pre-screening solution containing horseradish peroxidase (0.1 mg/mL), pyruvic acid (0.2 mg/mL) and 50 mM PBS (pH 8.0) was pre-soaked on filter paper. An NC membrane was paved on the filter paper and placed for 1 h at room temperature. The membrane was frozen with liquid nitrogen and then transferred to pre-soaked filter paper, which contained the colorimetric assay solution: 1×3,3'-diaminobenzidine tablets (Maclin), 10 mM substrate, horseradish peroxide enzyme (0.1 mg/mL) and 50 mM PBS (pH 8.0). The membrane was placed at room temperature. The change in color can be observed over time.

The single colonies whose colors changed on a corresponding mother plate were picked with a sterile toothpick and inoculated into a 96-well deep plate containing 1 mL of LB culture solution (containing 50 mg/mL and 100 mg/mL kanamycin) per well one by one, cultured for 8 hours at 37° C. and 200 r/min until the later stage of exponential growth was reached. 2004, of bacterial solution was taken from each well of the mother plate and inoculated into the corresponding well of a seed plate, 100 μL of glycerin (50%) was added into each well, and the above bacterial solution was evenly mixed and stored in a −80° C. medical refrigerator. The remaining bacterial solution in each well of the mother plate was supplemented with 200 μL of LB culture solution (containing 2.5 mM IPTG), induced for 20 hours at 25° C. and 150 r/min. After induction was ended, the mother plate was centrifuged for 120 min at 4500 r/min, and the bacteria were collected. The bacteria were washed twice with PBS (pH 8.0) buffer and centrifuged under the same conditions, and the supernatant was discarded. After being frozen overnight in an ultra-low temperature refrigerator, the mother plate was thawed for 30 min at room temperature, frozen for 20 min at an ultra-low temperature, and the freezing-thawing was repeated for three times. 250 μL of lysozyme (5 mg/mL) was added into each well of the mother plate to re-suspend the bacteria. The mother plate was subjected to constant-temperature incubation for 30 min at 37° C. and 200 r/min to fully lyse the cells to release intracellular enzymes, and then centrifuged for 10 min (4500 r/min) to separate a crude enzyme solution from the bacteria.

80 μL of supernatant (crude enzyme solution) was taken from each well of the mother plate and placed in the corresponding well of a 96-well microplate, and the 96-well microplate was sealed with a membrane and put in a PCR instrument to conduct constant-temperature treatment for 10 min at 50° C. and placed for 10 min in an ice bath. Each 20 μL of crude enzyme solution was mixed with 180 μL of substrate solution, and the enzyme activity of the crude enzyme solution for catalytic transamination reaction before and after thermal treatment was detected by a microplate reader, and the enzyme activity of a corresponding enzyme not subjected to thermal treatment was defined as 100%. The residual enzyme percentage of the crude enzyme solution subjected to thermal treatment was calculated, and mutons whose residual enzyme activity percentages were higher than those of wild types were selected. Finally, forward mutons whose residual enzyme activity percentages were on TOP10 were selected, activated and then sent to Anhui General Biological Company for sequencing and analysis.

6. Expression and Purification of Mutants

Some forward mutations with higher residual viability were obtained after about 3000 colonies were screened through the plate. *E. coli* BL 21 competent cells and transaminase mutant plasmids with correct sequencing were placed for 5 min in ice-water bath, 10 μL of plasmids were added into the competent cells, the plasmids and the competent cells were gently and evenly mixed, the obtained mixture was placed for 30 min on ice, subjected to heat shock for 90s in a 42° C. water bath pot and quickly put back for 3 min in ice bath, 600 μL of LB culture medium was added, and the above mixed solution was revived for 50 min at 37° C. and 180 r/min. 1504, of culture medium was evenly coated on a LB solid plate (containing 50 μg/mL kanamycin and 100 μg/mL ampicillin), cultured for 30 min in a 37° C. incubator, and then cultured overnight by reversing the plate.

The single colonies were picked, inoculated into a tube containing 5 mL of LB liquid culture medium, and cultured overnight at 37° C. and 200 r/min. The cultured bacterial solution was inoculated to 200 mL of LB culture medium containing 50 μg/mL kanamycin and 100 μg/mL ampicillin) in an inoculation amount of 1% ratio (volume ratio), cultured at 37° C. and 200 r/min until the value of $OD_{600}$ was 0.4~0.5, at this moment, a proper volume of IPTG (final concentration was 1 mmol/L) was added, the bacterial solution was subjected to induction culture for 18 hours at 16~30° C. and 150~200 r/min, and then the bacteria were collected.

The collected bacteria were washed twice with phosphate buffer and suspended in 50 ml of cell breaking buffer (50 mM sodium dihydrogen phosphate, 300 mM sodium chloride, 20 mM imidazole, and pH 8.0). Under the condition of ice bath, the bacterial cells were broken in a homogenizer. The cell breaking solution was centrifuged for 30 min at 12000 r/min and 4° C., and the supernatant was collected to obtain a crude enzyme solution containing ω-transaminase.

The crude enzyme solution was separated and purified by Ni-NTA affinity chromatography. After loading, cleaning and eluting, the eluent was collected and dialyzed to remove small molecules to obtain a pure enzyme. After being appropriately diluted, the concentration of the pure enzyme was determined by the Coomassie brilliant blue method. Specific purification steps:

(1) Equilibrium Ni-NTA affinity chromatography column: the column was washed with 3 column volumes of 20% ethanol, deionized water and 20 mM imidazole buffer, respectively;

(2) Loading: the crude enzyme solution was sucked with a syringe and filtered with the 0.45 μm filtration membrane, and a recombinant protein with 6 histidine tags was specifically bound to a filler;

(3) Washing: 2-3 column volumes of 50 mM imidazole buffer, and whether hybrid proteins were completely removed was detected by Bradford solution;

(4) Eluting: 5 mL of 100 mM elution buffer, and 5 mL of 250 mM elution buffer;

(5) Storing the column: the column was washed with 3 column volumes of 20 mM imidazole buffer, deionized water and 20% ethanol, respectively, and finally stored in 20% ethanol.

7. SDS-PAGE Analysis of Transaminase Mutants

A protein content standard curve was built by using an improved Bradford protein concentration determination kit to determine the concentration of the pure enzyme. The preparation steps of the protein standard curve refer to an instruction. The molecular weight and purity of the purified protein were identified by SDS-PAGE (12% separation gel and 5% concentrated gel).

Sample treatment: 40 μL of crude enzyme solution and 10 μL of 5× Protein sampling buffer were evenly mixed, and the obtained mixed solution was placed in boiling water bath for 10 min.

Loading: 5 μL of protein marker, and 104, of sample.

Electrophoretic conditions: conduct electrophoresis for about 45 min under the voltage of 170V, stop electrophoresis when bromine phenol blue indicator moved to a position distanced from the edge lower end of gel by about 1 cm.

Dyeing: a dying solution immersed the gel and heated for 1 min in a microwave oven, and then dying was conducted for 25 min in a shaking table.

Decolorization: the dyeing solution was recycled, a decolorization solution was used, and the decolorization solution changed every hour until protein bands were clear.

Figure 3:
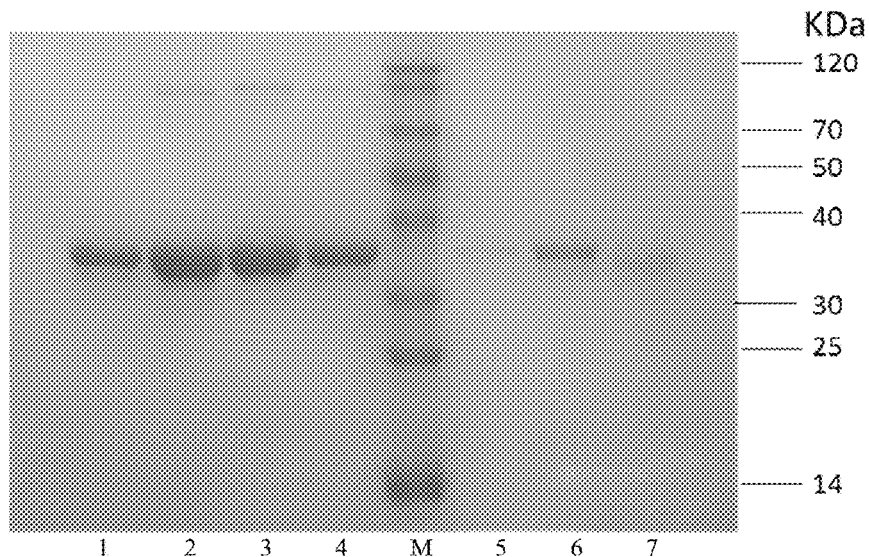
FIG. 3 is an SDS-PAGE electrophoretic analysis result graph of mutants, in which lanes are respectively as follows: M: protein marker; 1: F115L-H210N-E253A-I295V, 2:H210N-N245D-E253A-G292D, 3: I77L-E133A-N245D-G292D, 4:I77L-Q97E-F115L-L118T-E253A-G292D, 5: I77L-F115L-E133A-H210N-N245D, 6:F115L-H210N; and 7: F115L-H210N-M150C-M280C.

SDS-PAGE analysis of transaminase mutant 1118T is shown in FIG. 3. The molecular weight of the protein is close to a theoretical molecular weight 36.1 kDa of wild-type enzyme.

8. Concentration of Mutant Enzyme

The molecular weight of the transaminase was about 36.1 kDa. Generally, the molecular weight cut off was between ⅕ and ⅓ of a molecular weight of a target protein. A concentration tube with a molecular weight cut off of 10 kDa was selected.

Pretreatment of concentration tube: the concentration tube was washed with 20% ethanol, deionized water and PBS buffer (pH 8.0) successively, and centrifuged for 10 min at 4° C. and 4000 r/min.

Concentration of enzyme: 5 mL of enzyme to be concentrated was added into a concentration tube, centrifuged for 15-20 min at 4° C. and 4000 r/min until the volume of the enzyme solution was about 1 mL. Then, multiple volumes of PBS buffer (pH 8.0) were added, the resulting mixed solution was centrifuged for 20 min at 4° C. and 4000 r/min, and the step were repeated twice. The concentrated enzyme solution in the inner tube was taken and stored at a low temperature.

Posttreatment of concentration tube: the concentration tube was washed with PBS buffer, deionized water and 20% ethanol successively, centrifuged for 10 min at 4° C. and 4000 r/min, and finally 20% ethanol was added into the inner tube to immerse the upper end of the membrane, and the tube was stored in a 4° C. refrigerator.

9. Determination of Mutant Enzyme Activity

With (R)-(+)-α-methylbenzylamine and pyruvic acid were used as substrates, and a substrate solution was prepared from phosphate buffer (50 mm, pH 8.0). 200 μL of reaction system comprised 180 μL of substrate solution (0.25% DMSO, 2.5 mm (R)-(+)-α-methylbenzylamine, 2.5 mM pyruvic acid, and 0.1 mM PLP) and 20 μL of pure enzyme solution (about 0.3 mg/ml). The variation curve of an OD value with time at a wavelength of 245 nm was detected by a microplate reader. The calculation method of enzyme activity is shown in Formula 1:

$$U/mg = \frac{\Delta OD_{245} \cdot V}{d \cdot \varepsilon \cdot V_E \cdot [E]}$$

Wherein, $\Delta OD_{245}$: change in absorbance per minute at 245 nm; V: a total volume of an enzyme reaction system (200 μL); d: an optical diameter (0.6 cm); ε: a molar absorption coefficient of acetophenone (12000 L/(mol·cm)); $V_E$: a volume of an enzyme in the reaction system (20 μL); [E]: an concentration (mg/mL) of an enzyme. The results are shown in Table 2.

TABLE 2

Dynamic parameters of wild types and mutants

| Name | $K_{cat}^{pyruvate}$ (s$^{-1}$) | $K_m^{pyruvate}$ (mM) | $k_{cat}/K_m^{pyruvate}$ (L/(s·mmol)) | $k_{cat}^{\alpha\text{-}MBA}$ (s$^{-1}$) | $K_m^{\alpha\text{-}MBA}$ (mM) | $k_{cat}/K_m^{\alpha\text{-}MBA}$ (L/(s·mmol)) |
|---|---|---|---|---|---|---|
| WT-ATA | 0.50 ± 0.01 | 0.23 ± 0.02 | 2.22 | 0.64 ± 0.01 | 0.23 ± 0.03 | 2.82 |
| F115L-H210N-M150C-M280C | 3.87 ± 0.03 | 2.67 ± 0.02 | 1.45 | 1.85 ± 0.03 | 0.26 ± 0.01 | 7.12 |
| F115L-H210N | 2.55 ± 0.01 | 1.49 ± 0.02 | 1.71 | 1.98 ± 0.02 | 0.55 ± 0.02 | 3.6 |
| F115L-H210N-E253A-I295V | 3.17 ± 0.01 | 1.56 ± 0.07 | 2.03 | 2.48 ± 0.01 | 0.80 ± 0.03 | 3.1 |
| I77L-F115L-E133A-H210N-N245D | 1.96 ± 0.03 | 1.99 ± 0.02 | 0.99 | 1.44 ± 0.01 | 0.55 ± 0.01 | 2.62 |
| I77L-Q97E-F115L-L118T-E253A-G292D | 2.76 ± 0.01 | 2.08 ± 0.03 | 1.33 | 2.00 ± 0.01 | 0.84 ± 0.02 | 2.38 |
| I77L-E133A-N245D-G292D | 3.05 ± 0.02 | 2.59 ± 0.02 | 1.18 | 2.02 ± 0.05 | 0.84 ± 0.05 | 2.40 |
| H210N-N245D-E253A-G292D | 1.89 ± 0.03 | 0.63 ± 0.01 | 3.01 | 1.73 ± 0.01 | 0.32 ± 0.03 | 5.42 |

10. Determination of Thermal Stability Parameters of Mutant Enzyme

The purified wild enzyme and mutant enzyme were incubated for 10 min in 25-55° C. water bath, and then quickly cooled for 10 min on ice. The substrate solution was prepared from phosphate buffer (50 mmol/L and pH 8.0), 200 μL of reaction system comprised 180 μL of substrate solution (0.25% DMSO, 2.5 mmol/1 (R)-(+)-α-methylbenzylamine ((R)-α-MBA), 2.5 mmol/L pyruvic acid and 0.1 mmol/L PLP) and 20 μL of pure enzyme solution (about 0.3 mg/mL), and the corresponding enzyme activity of the enzyme at 245 nm was detected by MD190 microplate reader (Purmonen M, Valjakka J, Takkinen K, et al. Molecular dynamics studies on the thermostability of family 11 xylanases [J]. Protein engineering design and selection, 2007, 20 (11): 551-559).

The temperature was used as the abscissa and a ratio of enzyme activities after and after thermal treatment was used as the ordinate, and Boltzmann S-type function fitting was conducted by Origin 8.0 software to calculate the half-inactivation temperature ($T_{50}^{10}$).

The wild enzyme and the mutant enzyme were incubated for 2-50 min at 40° C. respectively. After incubation, the wild enzyme and the mutant enzyme were quickly cooled for 10 min. The enzyme activity was measured by the above method. Plotting was conducted by using time was used as the abscissa and using a ratio of specific activities before and after thermal treatment as the ordinate, the nonlinear equation $y=\exp(-K_d \cdot t)$ was fitted by Origin 8.0 software. The first-order rate constant ($k_d$) was determined by nonlinear regression, and the corresponding half-life period ($t_{1/2}$) when the enzyme activity decreased to 50% was calculated.

Figure 4:
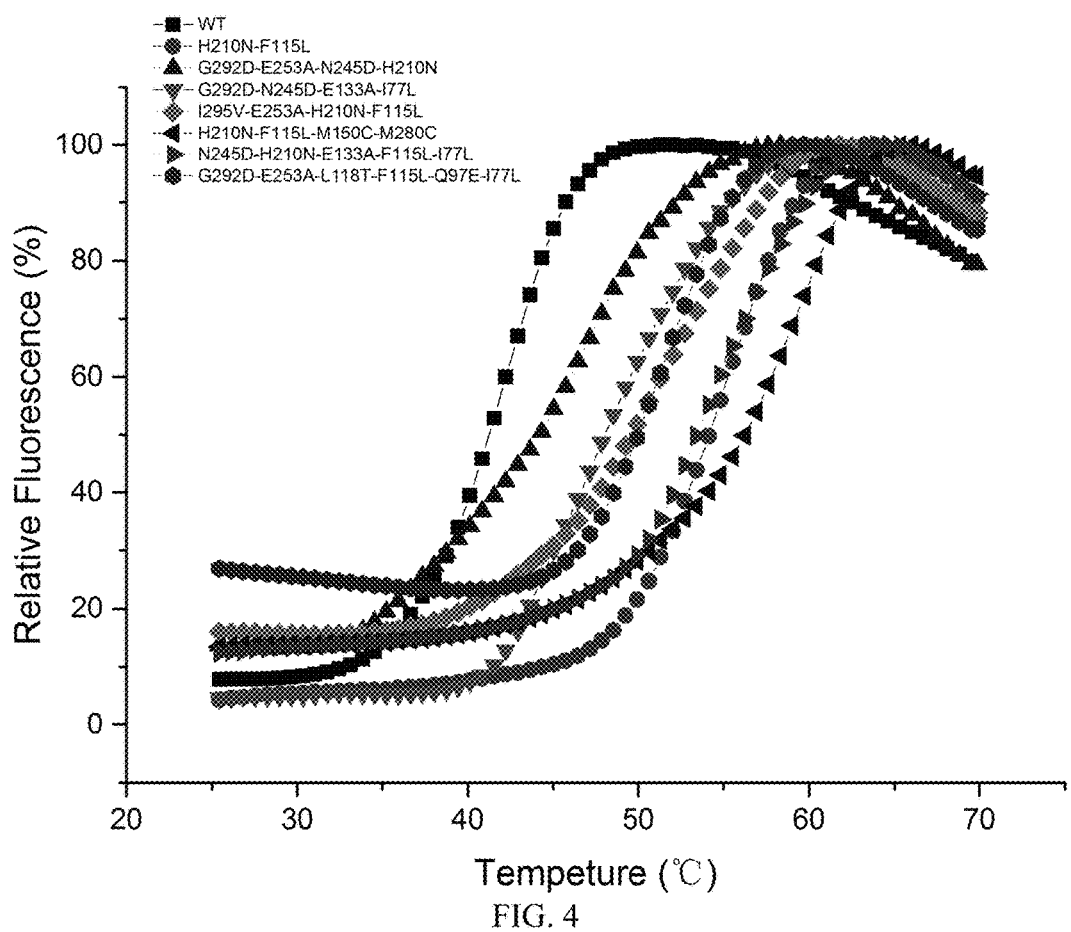
FIG. 4 shows half-life period $t_{1/2}$ results of different mutant enzymes and wide type enzymes in example 1.
Figure 5:
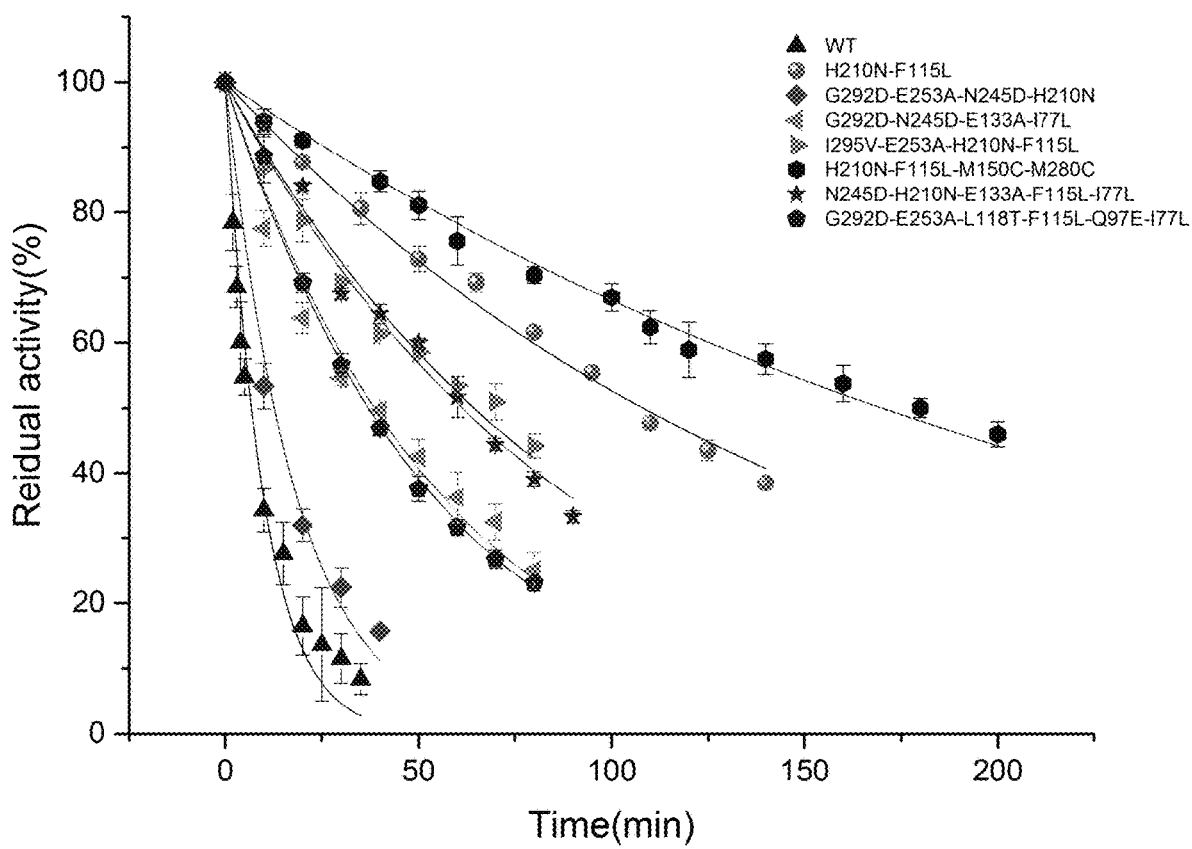
FIG. 5 shows half-inactivation temperature $T_{50}^{10}$ results of different mutant enzymes and wide type enzymes in example 1.

The experimental results are shown in Table 3, FIG. 4 and FIG. 5.

11. Characterization of Thermodynamic Stability of Mutant Enzyme

A differential scanning fluorometry (DSF) method is a rapid and low-cost method to study the stability of proteins and an interaction between proteins and small molecules. A pure enzyme to be analyzed (concentrated to remove imidazole) (0.1 mg/mL) and fluorescent dye SYPRO Orange dye 2× were properly diluted, 50 mM PBS buffer (pH 8.0) was mixed with 150 mM NaCl, total volume was 50 μL, an enzyme buffer was used as negative control, and three groups were measured for each sample in parallel. A PCR tube containing a sample to be analyzed was put into a real-time fluorescence quantitative PCR instrument for programmed temperature, and a temperature rising rate is 0.7° C./30s. The change of fluorescence intensity of enzyme samples from 25° C. to 70° C. was recorded by the real-time fluorescence quantitative PCR instrument. Where, an excitation wavelength was 490 nm and an emission wavelength was 605 nm. Plotting was conducted by fluorescence intensity vs. temperature, and the curve is S-shaped, wherein the inflection point of the curve is the pyrolysis folding temperature (Tm) of the protein.

The thermodynamic analysis of the enzyme adopts a two-state equilibrium model, and the Tm value is calculated according to Boltzmann Formula 2.

$$y = UF + \frac{(NF - UF)}{1 + e^{\frac{(Tm-x)}{\alpha}}}$$

Wherein, y represents fluorescence intensities at different temperatures, UF is a fluorescence intensity of an enzyme in a natural folding state, NF is the maximum fluorescence intensity in an unfolding state, x refers to a temperature, and dx is a slope of a relationship curve between the fluorescence intensity and the temperature. Fitting was conducted by software Origin 8.0 to obtain Tm.

TABLE 3

Stability parameters of wild types and mutants

| Name | $T_{50}^{15}$(° C.) | $t_{1/2}$(min) | $T_m$ |
|---|---|---|---|
| WT-ATA | 38.50 ± 0.50 | 6.90 ± 0.60 | 41.40 ± 0.20 |
| F115L-H210N-M150C-M280C | 52.20 ± 0.42 | 172.70 ± 3.68 | 55.30 ± 0.29 |
| F115L-H210N | 49.78 ± 0.50 | 101.20 ± 0.13 | 54.30 ± 0.25 |
| F115L-H210N-E253A-I295V | 47.86 ± 0.28 | 65.54 ± 1.00 | 50.00 ± 0.34 |
| I77L-F115L-E133A-H210N-N245D | 47.65 ± 0.22 | 60.80 ± 0.70 | 53.80 ± 0.28 |
| I77L-Q97E-F115L-L118T-E253A-G292D | 45.62 ± 0.44 | 41.68 ± 0.90 | 49.90 ± 0.13 |
| I77L-E133A-N245D-G292D | 44.81 ± 0.45 | 37.40 ± 2.40 | 48.70 ± 0.34 |
| H210N-N245D-E253A-G292D | 41.80 ± 0.53 | 12.55 ± 0.48 | 44.30 ± 0.33 |

Figure 6:
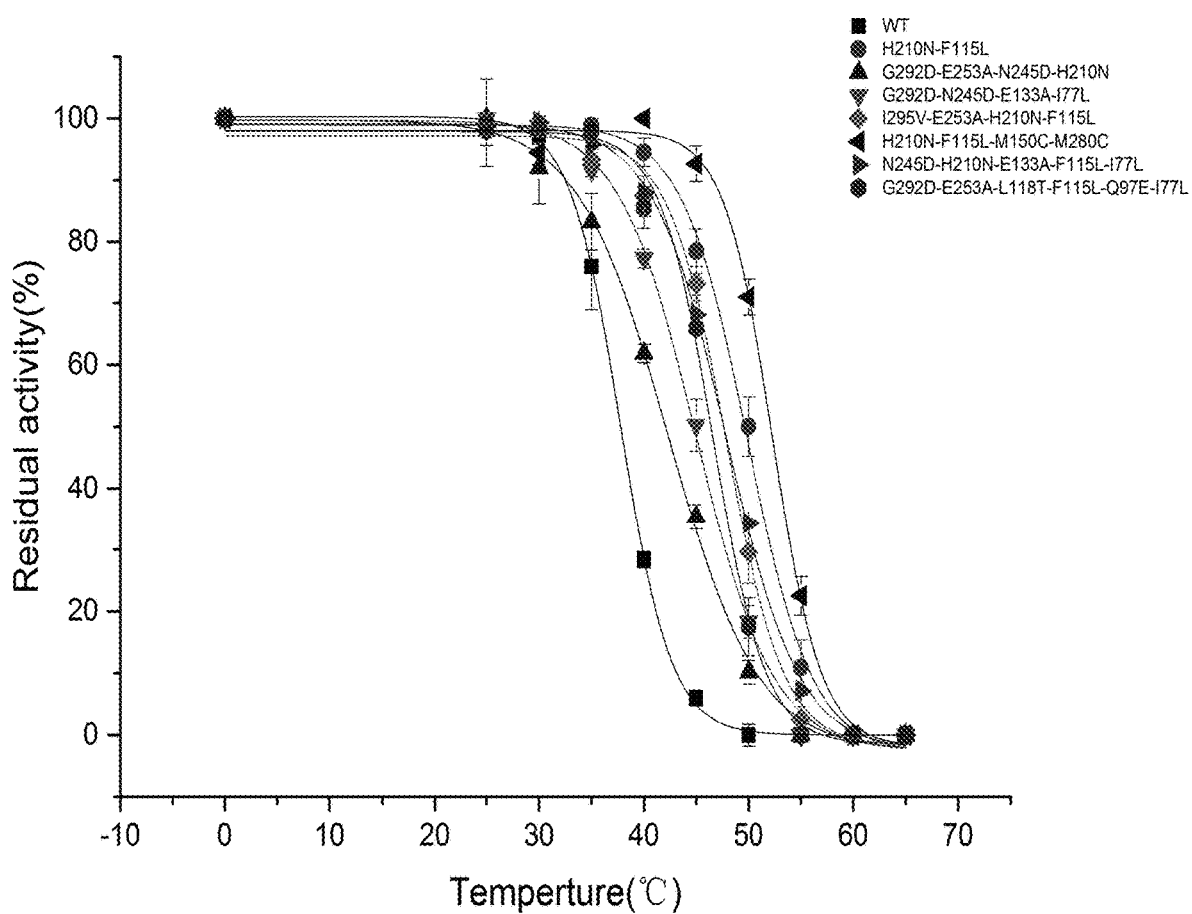
FIG. 6 shows pyrolysis folding results $T_m$ of transaminases and mutant enzymes thereof measured by a differential fluorescence scanning method.

Experimental results are shown in Table 3 and FIG. 6.

What is claimed is:

1. An ω-transaminase mutant obtained by DNA synthetic shuffling combined mutation, wherein the ω-transaminase mutant is obtained by point mutation of a wild type ω-transaminase from *Aspergillus terrus*, the amino acid sequence of the wild type ω-transaminase is shown in SEQ ID NO:1, and the ω-transaminase mutant comprises the amino acid sequence of SEQ ID NO: 1, except amino acid substitutions consisting of one of the following:

(1) F115L-H210N-M150C-M280C;
(2) F115L-H210N;
(3) F115L-H210N-E253A-I295V;
(4) I77L-F115L-E133A-H210N-N245D;
(5) I77L-Q97E-F115L-L118T-E253A-G292D;
(6) I77L-E133A-N245D-G292D; or
(7) H210N-N245D-E253A-G292D.

2. A method for catalyzing (R)-(+)-α-methylbenzylamine to produce acetophenone comprising the step of utilizing the ω-transaminase mutant according to claim 1.

3. A method for catalyzing (R)-(+)-α-methylbenzylamine to produce acetophenone comprising the step of using the ω-transaminase mutant according to claim 1 as a catalytic enzyme, wherein a reaction system comprises a substrate solution and an enzyme solution added into the substrate solution, the substrate solution and the enzyme solution being added in a volume ratio of 9:1, wherein the substrate solution comprises: 2.5 mM (R)-(+)-α-methylbenzylamine, 2.5 mM pyruvic acid and 0.1 mM PLP; the enzyme solution comprises 0.3 mg/mL catalytic enzyme; a reaction temperature is 25~55° C., and pH is 8.0.

4. The ω-transaminase mutant according to claim 1, wherein the amino acid substitutions consist of: F115L-H210N-M150C-M280C.

* * * * *